United States Patent
Caldwell et al.

(12) 
(10) Patent No.: US 6,525,065 B1
(45) Date of Patent: Feb. 25, 2003

(54) PHARMACEUTICAL COMPOSITIONS AND METHODS FOR EFFECTING DOPAMINE RELEASE

(75) Inventors: William Scott Caldwell, Winston-Salem, NC (US); Merouane Bencherif, Winston-Salem, NC (US); Gary Maurice Dull, Lewisville, NC (US); Peter Anthony Crooks, Lexington, KY (US); Patrick Michael Lippiello, Lewisville, NC (US)

(73) Assignee: Targacept, Inc., Winston-Salem, NC (US)

( * ) Notice: Subject to any disclaimer, the term of this patent is extended or adjusted under 35 U.S.C. 154(b) by 0 days.

(21) Appl. No.: 08/885,397

(22) Filed: Jun. 30, 1997

(51) Int. Cl.$^7$ ......................... A61K 31/46; C07D 453/02
(52) U.S. Cl. ......................... 514/305; 514/299; 514/300; 514/277; 514/256; 546/137
(58) Field of Search .................. 514/305, 299, 514/300, 256, 277; 546/137

(56) References Cited

U.S. PATENT DOCUMENTS

| | | |
|---|---|---|
| 5,346,906 A | 9/1994 | Baker et al. |
| 5,510,355 A | 4/1996 | Bencherif et al. .......... 514/305 |
| 5,559,124 A | 9/1996 | Bencherif et al. |
| 5,583,140 A | 12/1996 | Bencherif et al. |
| 5,597,919 A | 1/1997 | Dull et al. |
| 5,604,231 A | 2/1997 | Smith et al. |

FOREIGN PATENT DOCUMENTS

| | | | |
|---|---|---|---|
| EP | 0 412 798 A2 | 2/1991 | ......... C07D/453/02 |
| EP | 0 559 495 A1 | 9/1993 | ......... A61K/31/465 |
| WO | WO94/08992 | 4/1994 | |
| WO | WO95/03306 | 2/1995 | ......... C07D/487/08 |
| WO | WO96/36637 | 11/1996 | ......... C07D/471/08 |

OTHER PUBLICATIONS

Sadikov et al., "Syntheses Based on Anabasine," pp. 3345–3347 (1962).
Rubtsov et al., "Hofmann Cleavage of 6, 9–Diazoniadispiro–(5.2.5.2) Hexadecan Dichlorid with Methanolic Potassium Hydroxide," pp. 624–630 (1964).

*Primary Examiner*—Bennett Celsa
(74) *Attorney, Agent, or Firm*—Womble Carlyle Sandridge & Rice PLLC

(57) ABSTRACT

Patients susceptible to or suffering from disorders, such as central nervous system disorders, which are characterized by an alteration in normal neurotransmitter release, such as dopamine release (e.g., Parkinsonism, Parkinson's Disease, Tourette's Syndrome, attention deficit disorder, or schizophrenia) are treated by administering an endo or exo form of a 1-aza-2-(3-pyridyl)bicyclo[2.2.1]heptane, a 1-aza-2-(3-pyridyl)bicyclo[2.2.2]octane, a 1-aza-2-(3-pyridyl)bicyclo[3.2.2]nonane, a 1-aza-7-(3-pyridyl)bicyclo[2.2.1]heptane, a 1-aza-3-(3-pyridyl)bicyclo[3.2.2]nonane, or a 1-aza-7-(3-pyridyl)bicyclo[3.2.2]nonane.

11 Claims, No Drawings

PHARMACEUTICAL COMPOSITIONS AND METHODS FOR EFFECTING DOPAMINE RELEASE

BACKGROUND OF THE INVENTION

The present invention relates to pharmaceutical compositions, and particularly pharmaceutical compositions incorporating compounds which are capable of affecting nicotinic cholinergic receptors. The present invention also relates to methods for treating a wide variety of conditions and disorders, and particularly conditions and disorders associated with dysfunction of the central and autonomic nervous systems.

Nicotine has been proposed to have a number of pharmacological effects. See, for example, Pullan et al. *N. Engl. J. Med.* 330:811–815 (1994). Certain of those effects may be related to effects upon neurotransmitter release. See for example, Sjak-shie et al., *Brain Res.* 624:295 (1993), where neuroprotective effects of nicotine are proposed. Release of acetylcholine and dopamine by neurons upon administration of nicotine has been reported by Rowell et al., *J. Neurochem.* 43:1593 (1984); Rapier et al., *J. Neurochem.* 50:1123 (1988); Sandor et al., *Brain Res.* 567:313 (1991) and Vizi, *Br. J. Pharmacol.* 47:765 (1973). Release of norepinephrine by neurons upon administration of nicotine has been reported by Hall et al., *Biochem. Pharmacol.* 21:1829 (1972). Release of serotonin by neurons upon administration of nicotine has been reported by Hery et al., *Arch. Int. Pharmacodyn. Ther.* 296:91 (1977). Release of glutamate by neurons upon administration of nicotine has been reported by Toth et al., *Neurochem Res.* 17:265 (1992). In addition, nicotine reportedly potentiates the pharmacological behavior of certain pharmaceutical compositions used for the treatment of certain CNS disorders. See, Sanberg et al., *Pharmacol. Biochem. & Behavior* 46:303 (1993); Harsing et al., *J. Neurochem.* 59:48 (1993) and Hughes, *Proceedings from Intl. Symp. Nic.* S40 (1994). Furthermore, various other beneficial pharmacological effects of nicotine have been proposed. See, Decina et al., *Biol. Psychiatry* 28:502 (1990); Wagner et al., *Pharmacopsychiatry* 21:301 (1988); Pomerleau et al., *Addictive Behaviors* 9:265 (1984); Onaivi et al., *Life Sci.* 54(3):193 (1994) and Hamon, *Trends in Pharmacol. Res.* 15:36.

Various nicotinic compounds have been reported as being useful for treating a wide variety of conditions and disorders. See, for example, Williams et al. *DN&P* 7(4):205–227 (1994), Arneric et al., *CNS Drug Rev.* 1(1): 1–26 (1995), Arneric et al., *Exp. Opin. Invest. Drugs* 5(1):79–100 (1996), Bencherif et al., *JPET* 279:1413 (1996), Lippiello et al., *JPET* 279:1422 (1996), PCT WO 94/08992, PCT WO 96/31475, and U.S. Pat. Nos. 5,583,140 to Bencherif et al., U.S. Pat. No. 5,597,919 to Dull et al., and U.S. Pat. No. 5,604,231 to Smith et al. Nicotinic compounds are particularly useful for treating a wide variety of Central Nervous System (CNS) disorders.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses; and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a cholinergic deficiency, a dopaminergic deficiency, an adrenergic deficiency and/or a serotonergic deficiency. CNS disorders of relatively common occurrence include presenile dementia (early onset Alzheimer's disease), senile dementia (dementia of the Alzheimer's type), Parkinsonism including Parkinson's disease, Huntington's chorea, tardive dyskinesia, hyperkinesia, mania, attention deficit disorder, anxiety, dyslexia, schizophrenia and Tourette's syndrome.

Senile dementia of the Alzheimer's type (SDAT) is a debilitating neurodegenerative disease, mainly afflicting the elderly; characterized by a progressive intellectual and personality decline, as well as a loss of memory, perception, reasoning, orientation and judgment. One feature of the disease is an observed decline in the function of cholinergic systems, and specifically, a severe depletion of cholinergic neurons (i.e., neurons that release acetylcholine, which is believed to be a neurotransmitter involved in learning and memory mechanisms). See, Jones, et al., *Intern. J. Neurosci.* 50:147 (1990); Perry, *Br. Med. Bull.* 42:63 (1986); and Sitaram, et al., *Science* 201:274 (1978). It has been observed that nicotinic acetylcholine receptors, which bind nicotine and other nicotinic agonists with high affinity, are depleted during the progression of SDAT. See, Giacobini, *J. Neurosci. Res.* 27:548 (1990); and Baron, *Neurology* 36:1490 (1986). As such, it would seem desirable to provide therapeutic compounds which either directly activate nicotinic receptors in place of acetylcholine or act to minimize the loss of those nicotinic receptors.

Certain attempts have been made to treat SDAT. For example, nicotine has been suggested to possess an ability to activate nicotinic cholinergic receptors upon acute administration, and to elicit an increase in the number of such receptors upon chronic administration to animals. See, Rowell, *Adv. Behav. Biol.* 31:191 (1987); and Marks, *J. Pharmacol. Exp. Ther.* 226:817 (1983). It also has been proposed that nicotine can act directly to elicit the release of acetylcholine in brain tissue, to improve cognitive functions, and to enhance attention. See, Rowell, et al., *J. Neurochem.* 43:1593 (1984); Sherwood, *Human Psychopharm.* 8:155 (1993); Hodges, et al., *Bio. of Nic.* Edit. by Lippiello, et al., p. 157 (1991); Sahakian, et al., *Br. J. Psych.* 154:797 (1989); and U.S. Pat. No. 4,965,074 to Leeson and U.S. Pat. No. 5,242,935 to Lippiello et al. Other methods for treating SDAT have been proposed, including U.S. Pat. No. 5,212,188 to Caldwell et al. and U.S. Pat. No. 5,227,391 to Caldwell et al., European Patent Application No. 588,917 and PCT WO 96/30372. Another proposed treatment for SDAT is COGNEX®, which is a capsule containing tacrine hydrochloride, available from Parke-Davis Division of Warner-Lambert Company, which reportedly preserves existing acetylcholine levels in patients treated therewith.

Parkinson's disease (PD) is a debilitating neurodegenerative disease, presently of unknown etiology, characterized by tremors and muscular rigidity. A feature of the disease appears to involve the degeneration of dopaminergic neurons (i.e., which secrete dopamine). One symptom of the disease has been observed to be a concomitant loss of nicotinic receptors which are associated with such dopaminergic neurons, and which are believed to modulate the process of dopamine secretion. See, Rinne, et al., *Brain Res.* 54:167 (1991) and Clark, et al., *Br. J. Pharm.* 85:827 (1985). It also has been proposed that nicotine can ameliorate the symptoms of PD. See, Smith et al., *Rev. Neurosci.* 3(1):25 (1992).

Certain attempts have been made to treat PD. One proposed treatment for PD is SINEMET CR®, which is a sustained-release tablet containing a mixture of carbidopa and levodopa, available from The DuPont Merck Pharmaceutical Co. Another proposed treatment for PD is ELDEPRYL®, which is a tablet containing selefiline hydrochloride, available from Somerset Pharmaceuticals, Inc. Another proposed treatment for PD is PARLODEL®, which is a tablet containing bromocriptine mesylate, available from Sandoz Pharmaceuticals Corporation. Another method for treating PD and a variety of other neurodegenerative diseases has been proposed in U.S. Pat. No. 5,210,076 to Berliner et al.

Tourette's syndrome (TS) is an autosomal dominant neuropsychiatric disorder characterized by a range of neurological and behavioral symptoms. Typical symptoms include (i) the onset of the disorder before the age of 21 years, (ii) multiple motor and phonic tics although not necessarily concurrently, (iii) variance in the clinical phenomenology of the tics, and (iv) occurrence of quasi daily tics throughout a period of time exceeding a year. Motor tics generally include eye blinking, head jerking, shoulder shrugging and facial grimacing; while phonic or vocal tics include throat clearing, sniffling, yelping, tongue clicking and uttering words out of context. The pathophysiology of TS presently is unknown, however it is believed that neurotransmission dysfunction is implicated with the disorder. See, Calderon-Gonzalez et al., *Intern. Pediat.* 8(2):176 (1993) and Oxford Textbook of Medicine, Eds. Weatherall et al., Chapter 21.218 (1987).

It has been proposed that nicotine pharmacology is beneficial in suppressing the symptoms associated with TS. See, Devor et al., *The Lancet* 8670:1046 (1989); Jarvik, *British J. of Addiction* 86:571 (1991); McConville et al., *Am. J. Psychiatry* 148(6):793 (1991); Newhouse et al., *Brit. J. Addic.* 86:521 (1991); McConville et al., *Biol. Psychiatry* 31:832 (1992); and Sanberg et al., *Proceedings from Intl. Symp. Nic.* S39 (1994). It also has been proposed to treat TS using HALDOL®, which is haloperidol available from McNeil Pharmaceutical; CATAPRES®, which is clonidine available from Boehringer Ingelheim Pharmaceuticals, Inc., ORAP®, which is pimozide available from Gate Pharmaceuticals; PROLIXIN®, which is fluphenazine available from Apothecon Division of Bristol-Myers Squibb Co.; and KLONOPIN®, which is clonazepam available from Hoffmann-LaRoche Inc.

Attention deficit disorder (ADD) is a disorder which affects mainly children, although ADD can affect adolescents and adults. See, Vinson, *Arch. Fam. Med.* 3(5):445 (1994); Hechtman, *J. Psychiatry Neurosci.* 19(3):193 (1994); Faraone et al., *Biol. Psychiatry* 35(6):398 (1994) and Malone et al., *J. Child Neurol.* 9(2):181 (1994). Subjects suffering from the disorder typically have difficulty concentrating, listening, learning and completing tasks; and are restless, fidgety, impulsive and easily distracted. Attention deficit disorder with hyperactivity (ADHD) includes the symptoms of ADD as well as a high level of activity (e.g., restlessness and movement). Attempts to treat ADD have involved administration of DEXEDRINE®, which is a sustained release capsule containing dextroamphetamine sulfate, available from SmithKline Beecham Pharmaceuticals; RITALIN®, which is a tablet containing methylphenidate hydrochloride, available from Ciba Pharmaceutical Company; and CYLERT®, which is a tablet containing premoline, available from Abbott Laboratories. In addition, it has been reported that administration of nicotine to an individual improves that individual's selective and sustained attention. See, Warburton et al., *Cholinergive Control of Cognitive Resources, Europsychobiology,* Eds. Mendlewicz, et al., pp. 43–46 (1993) and Levin et al. *Psychopharmacology* 123:55–63 (1996).

Schizophrenia is characterized by psychotic symptoms including delusions, catatonic behavior and prominent hallucinations, and ultimately results in a profound decline in the psychosocial affect of the subject suffering therefrom. Traditionally, schizophrenia has been treated with KLONOPIN®, which is available as a tablet containing clonezepam, available from Hoffmann-LaRoche Inc.; THORAZINE®, which is available as a tablet containing chlorpromazine, available from SmithKline Beecham Pharmaceuticals; and CLORAZIL®, which is a tablet containing clozapine, available from Sandoz Pharmaceuticals. Such neuroleptics are believed to be effective as a result of interaction thereof with the dopaminergic pathways of the CNS. In addition, a dopaminergic dysfunction possessed by individuals suffering from schizophrenia has been proposed. See, Lieberman et al., *Schizophr. Bull.* 19:371 (1993) and Glassman, *Amer. J. Psychiatry* 150:546 (1993). Nicotine has been proposed as being effective in effecting neurotransmitter dysfunction associated with schizophrenia. See, Merriam et al., *Psychiatr. Annals* 23:171 (1993) and Adler et al., *Biol. Psychiatry* 32;607 (1992). See also Freedman et al., *Proc. Natl. Acad. Sci.* 94:587–592 (1997).

It would be desirable to provide a useful method for the prevention and treatment of a disorder by administering a nicotinic compound to a patient susceptible to or suffering from such a disorder. It would be highly beneficial to provide individuals suffering from certain disorders (e.g., CNS diseases) with interruption of the symptoms of those disorders by the administration of a pharmaceutical composition containing an active ingredient having nicotinic pharmacology and which has a beneficial effect (e.g., upon the functioning of the CNS), but which does not provide any significant associated side effects (e.g., increased heart rate and blood pressure attendant with interaction of that compound with cardiovascular sites). It would be highly desirable to provide a pharmaceutical composition incorporating a compound which interacts with nicotinic receptors, such as those which have the potential to effect the functioning of the CNS, but which compound when employed in an amount sufficient to effect the functioning of the CNS, does not significantly effect those receptor subtypes which have the potential to induce undesirable side effects (e.g., appreciable pressor cardiovascular effects and appreciable activity at skeletal muscle sites).

SUMMARY OF THE INVENTION

The present invention relates to methods for the prevention or treatment of disorders characterized by an alteration in normal neurotransmitter release, such as dopamine release. The present invention also relates to methods for the prevention or treatment of disorders, such as central nervous system (CNS) disorders, which are characterized by an alteration in normal neurotransmitter release. The methods involve administering to a subject an effective amount of an endo or exo form of a 1-aza-2-(3-pyridyl)bicyclo[2.2.1]heptane, a 1-aza-2-(3-pyridyl)bicyclo[2.2.2]octane, a 1-aza-2-(3-pyridyl)bicyclo[3.2.2]nonane, a 1-aza-7-(3-pyridyl)bicyclo[2.2.1]heptane, a 1-aza-3-(3-pyridyl)bicyclo[3.2.2]nonane, or a 1-aza-7-(3-pyridyl)bicyclo[3.2.2]nonane.

The present invention, in another aspect, related to a pharmaceutical composition comprising an effective amount of a compound of the present invention. Such a pharmaceutical composition incorporates a compound which, when employed in effective amounts, has the capability of interacting with relevant nicotinic receptor sites of a subject, and hence has the capability of acting as a therapeutic agent in the prevention or treatment of disorders characterized by an alteration in normal neurotransmitter release. Preferred pharmaceutical compositions comprise novel compounds of the present invention.

The pharmaceutical compositions of the present invention are useful for the prevention and treatment of disorders, such as CNS disorders, which are characterized by an alteration in normal neurotransmitter release. The pharmaceutical compositions provide therapeutic benefit to individuals suffering from such disorders and exhibiting clinical manifestations of such disorders in that the compounds within those compositions, when employed in effective amounts, have the potential to (i) exhibit nicotinic pharmacology and affect relevant nicotinic receptors sites (e.g., act as a pharmacological agonist to activate nicotinic receptors), and (ii) elicit neurotransmitter secretion, and hence prevent and suppress the symptoms associated with those diseases. In addition, the compounds are expected to have the potential to (i) increase the number of nicotinic cholinergic receptors of the brain of the patient, (ii) exhibit neuroprotective effects and (iii) when employed in effective amounts do not cause appreciable adverse side effects (e.g., significant increases in blood pressure and heart rate, significant negative effects upon the gastro-intestinal tract, and significant effects upon skeletal muscle). The pharmaceutical compositions of the present invention are believed to be safe and effective with regards to prevention and treatment of disorders, such as CNS disorders, which are characterized by an alteration in normal neurotransmitter release.

The foregoing and other aspects of the present invention are explained in detail in the detailed description and examples set forth below.

DETAILED DESCRIPTION OF THE INVENTION

The present invention relates to compounds having the general formula I:

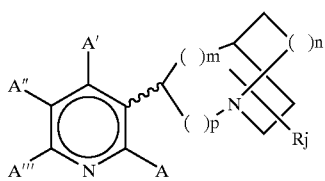

I where A, A', A" and A'" are individually substituent species characterized as having a sigma m value greater than 0, often greater than 0.1, and generally greater than 0.2, and even greater than 0.3; less than 0, generally less than −0.1; or 0; as determined in accordance with Hansch et al., *Chem. Rev.* 91:165 (1991); m, n and p are individually 0, 1 or 2, and the sum of p plus m is equal to 1 or 2 when n=0; R is a substituent other than hydrogen; j is an integer from 0 to 5, preferably 0 or 1, and most preferably 0; and the wavy line in the structure indicates that, depending upon the values of each of n, m, p and j, the compound can have the form of endo and exo isomers. The sum of m plus n plus p can vary, and typically is an integer from 1 to 4, with a sum of 1 to 3 being preferred. The identity of A, A', A" and A'" can vary, and each of those substituent species often has a sigma m value between about −0.3 and about 0.75, frequently between −0.25 and about 0.6. More specifically, examples of A, A', A" and A'" include H, F, Cl, Br, I, R', NR'R", $CF_3$, OH, CN, $NO_2$, $C_2R'$, SH, $SCH_3$, $N_3$, $SO_2CH_3$, OR', SR', C(=O)NR'R", NR'C(-O)R', C(=O)R', C(=O)OR', $(CH_2)_qOR'$, OC(=O)R', OC(=O)NR'R", and NR'C(=O) OR', where R' and R" are individually hydrogen or lower alkyl (e.g., $C_1$–$C_{10}$ alkyl, preferably $C_1$–$C_6$ alkyl, and more preferably methyl, ethyl, isopropyl or isobutyl), an aromatic group-containing species, and q is an integer from 1 to 6. In certain circumstances, it is preferred that the sigma m value of A" is not equal to 0. In addition, it is highly preferred that A is hydrogen, it is preferred that A' is hydrogen, and normally A'" is hydrogen. Generally, both A and A' are hydrogen, and A'" are all hydrogen; sometimes A and A' are hydrogen, and A'" is halo, OR', OH, NR'R", SH or SR'; and often A, A' and A'" are all hydrogen. For certain preferred compounds, A" is a non-hydrogen substitutent (i.e., such compounds are 5-substituted-3-pyridyl compounds). Typically, R is F, Cl, Br, I, R' as defined hereinbefore, $NO_2$ or an aromatic group-containing species. R' and R" can be straight chain or branched alkyl, or R' and R" can form a cycloalkyl functionality (e.g., cyclopropyl, cyclobutyl, cyclopentyl, cyclohexyl, cycloheptyl, adamantyl, quinuclidinyl). Representative aromatic group-containing species include pyrindinyl, quinolinyl, pyrimidinyl, phenyl, benzyl (where any of the foregoing can be suitably substituted with at least one substitutent group, such as alkyl, halo, or amino substituents). Representative aromatic ring systems are set forth in Gibson et al., *J. Med. Chem.* 39:4065 (1996). For NR'R', the nitrogen and R' and R" can form a ring structure, such as aziridinyl, azetidinyl, pyrrolidinyl, piperidinyl, piperazinyl or morpholinyl. Typically, R is positioned at a carbon bridgehead of the azabicyclo moiety, at a carbon adjacent to the carbon or nitrogen bridgehead of the azabicyclo moiety, or at the carbon adjacent to the carbon bearing the pyridyl substituent. The compounds represented in general formula I are optically active.

A representative compound is a 1-aza-2-(3-pyridyl) bicyclo[2.2.1]heptane, which can have an endo or exo form, and for which n=0, m=1 and p=0. A representative compound is a 1-aza-2-(3-pyridyl)bicyclo[2.2.2]octane, for which n-1, m=1 and p=0. A representative compound is a 1-aza-2-(3-pyridyl)bicyclo[3.2.2]nonane, for which n=1, m=2 and p=0. A representative compound is a 1-aza-7-(3-pyridyl)bicyclo[2.2.1]heptane, for which n=1, m=0 and p=0. A representative compond is a 1-aza-3-(3-pyridyl)bicyclo [3.2.2]nonane, for which n=1, m=1 and p=1. A representative compound is a 1-aza-7-(3-pyridyl)bicyclo[3.2.2] nonane, for which n=2, m=1 and p=0.

The manner in which certain 5-substituted-3-pyridyl compounds of the present invention can be synthetically produced can vary. For example, 5-bromo-3-pyridyl containing compounds can be prepared using a combination of synthetic techniques known in the art. 5-bromo substituted analogues of endo and exo 1-aza-2-(3-pyridyl)bicyclo[2.2.1] heptane, 1-aza-2-(3-pyridyl)bicyclo[2.2.2]octane, a 1-aza-2-(3-pyridyl)bicyclo[3.2.2]nonane, 1-aza-7-(3-pyridyl)bicyclo [2.2.1]heptane, 1-aza-3-(3-pyridyl)bicyclo[3.2.2]nonane, or 1-aza-7-(3-pyridyl)bicyclo[3.2.2]nonane can all be prepared starting from 5-bromonicotinic acid, which is commercially available from Aldrich Chemical Co. The 5-bromonicotinic acid is converted to the mixed anhydride with ethyl chloroformate and reduced with lithium aluminum hydride/ tetrahydro furan (THF) at −78° C., to afford 5-bromo-3-hydroxymethylpyridine, as reported by Ashimori et al., *Chem. Pharm. Bull.* 38:2446 (1990). Alternatively, the 5-bromonicotinic acid is esterified in the presence of sulfuric acid and ethanol, and the intermediate ester is reduced with sodium borohydride to yield 5-bromo-3-hydroxymethylpyridine, according to the techniques reported in C. F. Natatis, et al., *Org. Prep. and Proc. Int.* 24:143 (1992). The resulting 5-bromo-3-hydroxymethylpyridine can then be converted to the 5-bromo-3-aminomethylpyridine utilizing a modification of the techniques of O. Mitsunobu, *Synthesis* 1 (1981), or via treatment of 5-bromo-3-hydroxymethylpyridine with thionyl chloride and reaction of the resulting 5-bromo-3-chloromethylpyridine with aqueous ammonia/ethanol, according to North et al., WO 95/28400. 5-Bromo-3-aminomethylpyridine can be converted to 5-(1-azabicyclo[2.2.2]oct-2-yl)-3-(bromo)pyridine using methods described in U.S. Pat. No. 5,510,355 to Bencherif et al., the disclosures of which are hereby incorporated by reference in its entirety.

The manner in which the 5-bromo-3-pyridyl analogues of exo- and endo 1-aza-2-(3-pyridyl)bicyclo[2.2.1]heptane and 1-aza-7-(3-pyridyl)bicylo[2.2.1]heptane of the present invention can be synthetically prepared is analogous to the synthesis of the corresponding unsubstituted parent compounds (see, U.S. Pat. No. 5,510,355 to Bencherif et al.), except that 5-bromo-3-aminomethylpyridine is utilized instead of 3-aminomethylpyridine, in the formation of the Schiff base from the reaction with benzophenone. Thereafter, the 5-bromo Schiff base is subjected to the same procedures as described for the preparation of the unsubstituted parent compounds.

The manner in which 1-aza-3-(3-pyridyl)bicyclo[3.2.2]nonane and its 5-bromo-3-pyridyl analogue can be prepared is analogous to the synthesis of 1-aza-2-(3-pyridyl)bicyclo[2.2.2]octane and its 5-bromo-3-pyridyl analogue. The ethyl ester of the appropriate 3-pyridyl acetic acid is reacted with 4-mesyloxymethylpyran (or 4-chloromethylpyran, or 4-bromomethylpyran, or even 4-iodomethylpyran) in the presence of lithium diisopropyl amide (LDA), and the resulting 2-(3-pyridyl)-2-(4-pyranomethyl)-acetic acid ethyl ester converted to the corresponding carboxamide by treatment with ethanolic amino-1-(4-pyranomethyl)-2-(3-pyridyl)-ethane. This product is then subjected to the same procedures as described in U.S. Pat. No. 5,510,355 to Bencherif et al., for the synthesis of 1-aza-2-(3-pyridyl) bicyclo[2.2.2]octane.

The manner in which 1-aza-7-(3-pyridyl)bicyclo[3.2.2]nonane and its 5-bromo analogue can be prepared is analogous to the synthesis of 2-3-pyridyl)-1-azabicyclo[2.2.2]octane and its 5-bromo analogue, except that after the appropriate 3-aminomethylpyridine is converted to the Schiff base via reaction with benzophenone, the product is reacted with 4-(mesyloxymethyl)-oxepane [or 4-(chloromethyl)-oxepane, or 4-(bromomethyl)-oxepane, or even 4-(iodomethyl)-oxepane] in the presence of LDA, and thereafter, the product of this reaction is subjected to the same procedures as described in U.S. Pat. No. 5,510,355 to Bencherif et al., for the synthesis of 2-(3-pyridyl)-1-azabicyclo[2.2.2]octane.

The manner in which 1-aza-2-(3-pyridyl)bicyclo[3.2.2]nonane and its 5-bromo-3-pyridyl analogue can be prepared is analogous to the synthesis of 1-aza-2-(3-pyridyl)bicyclo[2.2.2]octane and its 5-bromo-3-pyridyl analogue, except that after the appropriate 3-aminomethylpyridine is converted to the Schiff base via reaction with benzophenone, the product is reacted with 4-mesyloxyethylpyran (or 4-chloroethylpyran, or 4-bromoethylpyran, or even 4-iodoethylpyran) in the presence of LDA, and thereafter, the product of this reaction is subjected to the same procedures as described in U.S. Pat. No. 5,510,355 to Bencherif et al., for the synthesis of 1-aza-3-(3-pyridyl)bicyclo [2.2.2] octane.

A representative synthetic technique for producing 1-aza-2-(3-pyridyl)bicyclo[3.2.2]nonane is as follows:

A solution of diisopropyl amine (1.05 ml, 10.39 mmol) in dry THF(25 ml) was added to n-butyllithium (6.4 ml, 1.6 M solution in THF) at 0° C.; this mixture is then added to a stirred suspension of the Schiff base obtained from the reaction of isopropylamine with 3-acetylpyridine [De Kimpe et al., *Tetrahedron Lett.*, 34, 4693–4696, 1993 ] (1 g, 6.1 mmol) in dry THF (20 ml) at 0° C. LDA is added to the mixture through a cannula, and the reaction is stirred for 45 mins at 0° C. Tetrahydropyran-4-methanyl bromide [Alfred Burger., J. Am. Chem. Soc., 72, 5512–5214] (1.21 g, 6.79 mmol) in dry THF at 0° C. is added to lithiated Schiff base. The reaction mixture is allowed to warm to ambient temperature, followed by additional stirring for 12 hrs. The reaction mixture is quenched with dilute hydrochloric acid (10%, 20 ml) and extracted with chloroform (3×40 ml). The combined organic extracts are dried over anhydrous potassium carbonate. Removal of solvent on a rotary evaporator and purification by silica gel column chromatography furnishes 3-(4-oxanyl)-1-(3-pyridyl)-propan-1-one as a pale yellow colored syrup. (1.14 g, 85%). To a stirred solution of 3-(4-oxanyl)-1 -(3-pyridyl)-propan-1-one (600 mg, 2.73 mmol) in saturated sodium bicarbonate solution (20 mL) is added hydroxylamine hydrochloride (1.87 g, 27.3 mmol). The reaction mixture is stirred at ambient temperature for 10 hrs. The reaction mixture is extracted with chlroform (4×25mL), and the chloroform extracts dried over anhydrous potassium carbonate. Removal of solvent on a rotary evaporator yields a mixture of the Z and E isomers of 1-(hydroxyimino)-3-(4-oxanyl)-1-(3-pyridyl)-propane as a thick, light brown colored syrup, which solidifies on standing (577 mg, 90.1%). To a stirred suspension of 1-(hydroxyimino)-3-(4-oxanyl)-1-(3-pyridyl)-propane (500 mg, 2.14 mmol) in ethanol (9520 mL), is added acetic acid (8 mL) at ambient temperature over a period of 15 minutes. Zinc dust (6 g) is added to this suspension, and the mixture refluxed for 4 h. The reaction mixture is cooled to room temperature and filtered through a celite pad. The filtrate is concentrated on a rotary evaporator to afford a white solid, which is dissolved in aqueous sodium hydroxide (50%, 10 mL). The resulting aqueous solution is extracted with chloroform (6×25 mL), and the combined extracts are dried over anhydrous potassium carbonate. Removal of solvent on a rotary evaporator furnishes 3-(4-oxanyl)-1-(3-pyridyl)-propylamine as thick colorless liquid (440 mg, 88.2%). 3-(4-Oxanyl)-1-(3-pyridyl)-propylamine (400 mg, 1.82 mmol) is dissolved in aqueous hydrobromic acid (48%, 10 mL) and the solution is carefully transferred to a sealed glass tube. The mixture is then saturated with HBr by bubbling HBr gas through the solution. The tube is then sealed and heated at 120° C. for 10 hrs. The reaction mixture is cooled to ambient temperature, and the residual HBr is removed on a rotary evaporator to afford a brown solid. The solid is dissolved in absolute ethyl alcohol (250 mL), anhydrous potassium carbonate (4 g) is added, and the mixture is refluxed for 10 h. The reaction mixture is then filtered through a celite pad and the filtrate is concentrated. The crude product thus obtained is purified by column chromatography on silica gel, using chloroform:methanol (9:1) as eluting solvent, to afford 1-aza-2-(3-pyridyl)bicyclo[3.2.2] nonane (258 mg, 70.25%) as a light tan oil. The free base is converted to the dihydrochloride, which is obtained as an off-white crystalline solid.

A number of analogues substituted at C-5 of the pyridine ring in the aforementioned compounds can be prepared from the corresponding 5-bromo compound. For example, 5-amino substituted compounds and 5-alkylamino substituted compounds can be prepared from the corresponding 5-bromo compound using the general techniques described in C. Zwart, et al., *Recueil Trav. Chim. Pays-Bas* 74:1062 (1955). 5-Alkoxy substituted analogues can be prepared from the corresponding 5-bromo compound using the general techniques described in D. L. Comins, et al., *J. Org. Chem.* 55:69 (1990) and H. J. Den Hertog et al., *Recl. Trav. Chim. Pays-Bas* 74:1171 (1955). 5-Ethynyl-substituted compounds can be prepared from the appropriate 5-bromo compound using the general techniques described in N. D. P. Cosford et al., *J. Med. Chem.* 39:3235 (1996). The 5-ethynyl analogues can be converted into the corresponding 5-ethenyl, and subsequently the corresponding 5-ethyl analogues by successive catalytic hydrogenation reactions using techniques known to those skilled in the art of organic synthesis. 5-Azido substituted analogues can be prepared from the corresponding 5-bromo compound by reaction with sodium azide in dimethylformamide using techniques known in the art of organic synthesis. 5-Alkylthio substituted analogues can be prepared from the corresponding 5-bromo compound by reaction with an appropriate alkylmercaptan in the presence of sodium using techniques known to those skilled in the art of organic synthesis.

A number of 5-substituted analogues of the aforementioned compounds can be synthesized from the corresponding 5-amino compounds via the 5-diazonium intermediate. Among the other 5-substituted analogues that can be produced from 5-diazonium intermediates are: 5-hydroxy analogues, 5-fluoro analogues, 5-chloro analogues, 5-bromo analogues, 5-iodo analogues, 5-cyano analogues, and 5-mercapto analogues. These compounds can be synthesized using the general techniques set forth in Zwart et al., supra. For example, 5-hydroxy substituted analogues can be prepared from the reaction of the corresponding 5-diazonium intermediate with water. 5-Fluoro substituted analogues can be prepared from the reaction of the 5-diazonium intermediate with fluoroboric acid. 5-Chloro substituted analogues can be prepared from the reaction of the 5-amino compound with sodium nitrite and hydrochloric acid in the presence of copper chloride. 5-Cyano substituted analogues can be prepared from the reaction of the corresponding 5-diazonium intermediate with potassium copper cyanide. 5-Amino substituted analogues can also be converted to the corresponding 5-nitro analogue by reaction with fuming sulfuric acid and peroxide, according to the general techniques described in Y. Morisawa, *J. Med. Chem.* 20:129 (1977) for converting an aminopyridine to a nitropyridine. Appropriate 5-diazonium intermediates can also be used for the synthesis of mercapto substituted analogues using the general techniques described in J. M. Hoffman et al., *J. Med. Chem.* 36:953 (1993). The 5-mercapto substituted analogues can in turn be converted to the 5-alkylthio substituted analogues by reaction with sodium hydride and an appropriate alkyl bromide using techniques known to those skilled in the art of organic synthesis. 5-Acylamido analogues of the aforementioned compounds can be prepared by reaction of the corresponding 5-amino compounds with an appropriate acid anhydride or acid chloride using techniques known to those skilled in the art of organic synthesis.

5-hydroxy substituted analogues of the aforementioned compounds can be used to prepare corresponding 5-alkanoyloxy substituted compounds by reaction with the appropriate acid, acid chloride, or acid anhydride, using techniques known to those skilled in the art of organic synthesis.

5-cyano substituted analogues of the aforementioned compounds can be hydrolyzed using techniques known to those skilled in the art of organic synthesis to afford the corresponding 5-carboxamido substituted compounds. Further hydrolysis results in formation of the corresponding 5-carboxylic acid substituted analogues. Reduction of the 5-cyano substituted analogues with lithium aluminum hydride yields the corresponding 5-aminomethyl analogue.

5-acyl substituted analogues can be prepared from corresponding 5-carboxylic acid substituted analogues by reaction with an appropriate alkyl lithium using techniques known to those skilled in the art.

5-carboxylic acid substituted analogues of the aforementioned compounds can be converted to the corresponding ester by reaction with an appropriate alcohol, according to methods known in the art of organic synthesis. Compounds with an ester group at the 5-pyridyl position can be reduced with sodium borohydride or lithium aluminum hydride using techniques known in the art of organic synthesis, to produce the corresponding 5-hydroxymethyl substituted analogue. These analogues in turn can be converted to compounds bearing an ether moiety at the 5-pyridyl position by reaction with sodium hydride and an appropriate alkyl halide, using conventional techniques. Alternatively, the 5-hydroxymethyl substituted analogues can be reacted with tosyl chloride to provide the corresponding 5-tosyloxymethyl analogue. The 5-carboxylic acid substituted analogues can also be converted to the corresponding 5-alkylaminoacyl analogue by reaction with an appropriate alkylamine and thionyl chloride, using techniques known to those skilled in the art. 5-Acyl substituted analogues of the aforementioned compounds can be prepared from the reaction of the appropriate 5-carboxylic acid substituted compound with an appropriate alkyl lithium salt, using techniques known to those skilled in the art of organic synthesis.

5-tosyloxymethyl substituted analogues of the aforementioned compounds can be converted to the corresponding 5-methyl substituted compounds by reduction with lithium aluminum hydride, using techniques known to those skilled in the art of organic synthesis. 5-Tosyloxymethyl substituted analogues of the aforementioned compounds can also be used to produce 5-alkyl substituted compounds via reaction with an alkyl lithium salt using techniques known to those skilled in the art of organic synthesis.

5-hydroxy substituted analogues of the aforementioned compounds can be used to prepare 5-N-alkylcarbamoyloxy substituted compounds by reaction with N-alkylisocyanates using techniques known to those skilled in the art of organic synthesis. 5-Amino substituted analogues of the aforementioned compounds can be used to prepare 5-N-alkoxycarboxamido substituted compounds by reaction with alkyl chloroformate esters, using techniques known to those skilled in the art of organic synthesis.

Analogous chemistries to the ones described hereinbefore for the preparation of the 5-substituted analogues of the azabicyclo analogues can be devised for the synthesis of 2-,4-, and 6-substituted analogues, utilizing the appropriate 2-, 4-, or 6-aminopyrdyl intermediate, followed by diazotization to the corresponding diazonium salt, and then utilizing the same procedures for introducing the variety of substituents into the pyridine ring as was described for the 5-substituted analogues above. Similarly, by utilizing 2, 4 or 6-bromopyridyl derivatives of the above azabicyclo analogues, and subjecting each of these derivatives to the same procedures as described for introducing 5-substituents into the pyridyl ring from appropriate 5-bromo precursors of these azabicyclo analogues, additional 2-, 4- or 6-substituents can be obtained in the manner described above.

Chiral auxiliary reagents that have been reported in the literature can be utilized in the synthesis of the pure enantiomers of the aforementioned exo and endo forms of 1-aza-2-(3-pyridyl)bicyclo[2.2.1]heptane, 1-aza-2-(3-pyridyl)bicyclo[2.2.2]octane, 1-aza-2-(3-pyridyl)bicyclo[3.2.2]nonane, 1-aza-7-(3-pyridyl)bicyclo[2.2.1]heptane, 1-aza-7-(3-pyridyl)bicyclo[3,2,2]nonane, or 1-aza-3-(3-pyridyl)bicyclo[3.2.2]nonane, D. Enders and U. Reinhold, *Liebigs Ann.* 11 (1996); D. Enders and D. L. Whitehouse, *Synthesis* 622 (1996)). One approach can be carried out using (+)-2-amino-3-phenylethanol (or its (−)-enantiomer), which is reacted with an appropriately substituted 3-pyridine carboxaldehyde in the presence of an optically pure amino acid as a chiral auxiliary agent, followed by treatment with the required pyrano magnesium bromide reagent and N-deprotection (via hydrogenolysis), to afford the chirally pure pyrano precursors of the aforementioned azabicyclo compounds. A second alternative method is the use of the chiral auxiliary agent, (S)-1-amino-2-methyloxymethylpyrrolidine (SAMP) or (S)-1-amino-2-(1-methoxy-1-methylethyl)-pyrrolidine (SADP), or their respective R-isomers, by reaction with an appropriately substituted 3-pyridine carboxaldehyde to form the corresponding oxime. Treatment of the oxime with the required pyrano magnesium bromide, followed by deprotection with sodium/liquid ammonia will afford the appropriate chirally pure pyrano precursor of the aforementioned azabicyclo compounds. A third alternative method is the use of (+) or (−)-a-pinanone in place of benzophenone in the formation of the appropriate precursor Schiff base used in the synthesis of the aforementioned azabicyclo compounds. See, U.S. Pat. No. 5,510,355 to Bencherif et al. For example, (+)-a-pinanone is reacted with an appropriately substituted 3-aminomethylpyridine to form the corresponding Schiff base, which is then utilized in place of the corresponding N-diphenylmethylidene-3-aminomethylpyridine, by reaction with the requisite halo or mesyl pyrano intermediate in the presence of LDA, followed by N-deprotection in $NH_2OH$/acetic acid, to afford the appropriate chirally pure pyrano precursor of the aforementioned azabicyclo compounds.

In the case of the exo- and endo 1-aza-2-(3-pyridyl)bicyclo[2.2.1]heptanes, use of the above enantioselective synthetic procedures will generate isomers with defined stereochemistry at C-2 and C-4 of the 1-azabicyclo[2.2.1]heptane ring; for example, one optical form of the chiral auxilliary agent that is utilized will afford chromatographically separable 2R,4S- and 2R,4R- exo- and endo-isomers of 1-aza-2-(3-pyridyl)bicyclo[2.2.1]heptanes while the other optical isomer of the chiral auxilliary agent will afford the chromatographically separable 2S,4R- and 2S,4S-exo- and endo-isomers of 1-aza-2-(3-pyridyl)bicyclo[2.2.1]heptanes.

The present invention relates to methods of effecting the release of neurotransmitters, such as dopamine, and to methods for providing the prevention of disorders characterized by an alteration of normal neurotransmitter release, such as dopamine release, in a subject susceptible to such a disorder, and for providing treatment to a subject suffering from a disorder. In particular, the method comprises administering to a patient an amount of a compound effective for providing some degree of prevention of the progression of a disorder such as a CNS disorder (i.e., provide protective effects), amelioration of the symptoms of the disorder, and/or amelioration of the reoccurrence of the disorder. In particular, the methods of the present invention comprise administering to a patient in need thereof, an amount of a compound selected from the group of compounds of general formula I hereinabove, which amount is effective to prevent or treat the disorder affecting the patient. The present invention further relates to pharmaceutical compositions incorporating the compounds of general formula I above. The compounds can be employed as racemic mixtures or as enantiomers.

The compounds can be employed in a free base form or in a salt form (e.g., as pharmaceutically acceptable salts). Examples of suitable pharmaceutically acceptable salts include inorganic acid addition salts such as hydrochloride, hydrobromide, sulfate, phosphate, and nitrate; organic acid addition salts such as acetate, propionate, succinate, lactate, glycolate, malate, tartrate, citrate, maleate, fumarate, methanesulfonate, salicylate, p-toluenesulfonate, and ascorbate; salts with acidic amino acids such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N-dibenzylethylenediamine salt; and salts with basic amino acids such as the lysine salt and arginine salts. The salts may be in some cases be hydrates or ethanol solvates.

A variety of conditions and disorders can be treated in accordance with the present invention. See, for example, PCT WO 94/08992 and PCT WO 96/31475, and U.S. Pat. No. 5,583,140 to Bencherif et al., U.S. Pat. No. 5,597,919 to Dull et al. and U.S. Pat. No. 5,604,231 to Smith et al. Central nervous systems disorders which can be treated in accordance with the methods of the present invention include CNS disorders associated with the alteration of normal neurotransmitter release, such as dopamine, in the brain, including conditions such as Parkinsonism, Parkinson's Disease, Tourette's Syndrome, attention deficit disorder, schizophrenia, and senile dementia of the Alzheimer's type.

The pharmaceutical compositions of the present invention can also include various other components as additives or adjuncts. Exemplary pharmaceutically acceptable components or adjuncts which are employed in relevant circumstances include antioxidants, free radical scavenging agents, peptides, growth factors, antibiotics, bacteriostatic agents, immunosuppressives, buffering agents, anti-inflammatory agents, anti-pyretics, time release binders, anaesthetics, steroids and corticosteroids. Such components can provide additional therapeutic benefit, act to affect the therapeutic action of the pharmaceutical composition, or act towards preventing any potential side effects which may be posed as a result of administration of the pharmaceutical composition. In certain circumstances, a compound of the present invention can be employed as part of a pharmaceutical composition with other compounds intended to prevent or treat a particular disorder.

The manner in which the compounds are administered can vary. The compounds can be administered by inhalation (e.g., in the form of an aerosol either nasally or using delivery articles of the type set forth in U.S. Pat. No. 4,922,901 to Brooks et al.); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); or transdermally (e.g., using a transdermal patch). Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time release capsule. As another example, the compounds can be delivered transdermally using the types of patch technologies available from Novartis and Alza Corporation. The administration of the pharmaceutical compositions of the present invention can be intermittent, or at a gradual, continuous, constant or controlled rate to a warm-blooded animal, (e.g., a mammal such as a mouse, rat, cat, rabbit, dog, pig, cow, or monkey); but advantageously is preferably administered to a human being. In addition, the time of day and the number of times per day that the pharmaceutical formulation is administered can vary. Administration preferably is such that the active ingredients of the pharmaceutical formulation interact with receptor sites within the body of the subject that effect the functioning of the CNS. More specifically, in treating a CNS disorder administration preferably is such so as to optimize the effect upon those relevant receptor subtypes which have an effect upon the functioning of the CNS, while minimizing the effects upon receptor subtypes in muscle and ganglia. Other suitable methods for administering the compounds of the present invention are described in U.S. Pat. No. 5,604,231 to Smith et al., the disclosure of which is incorporated herein by reference in its entirety.

Compounds of the present invention bind to relevant receptors and, are very potent (i.e., effect relevant receptor subtypes at low concentrations), and are very efficacious (i.e., significantly affect relevant receptor subtypes by activating those receptor subtypes to a high degree). Concentrations, determined as the amount of compound per volume of receptor-containing tissue, typically provide a measure of the degree to which that compound binds to and affects relevant receptor subtypes. The compounds of the present invention are selective in that at relevant concentrations (i.e., low concentrations) those compounds bind to, and have an affect upon, receptors associated with the release of neurotransmitters, e.g., dopamine, within the CNS.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder. Thus, when treating a CNS disorder, an effective amount of compound is an amount sufficient to pass across the blood-brain barrier of the subject, to bind to relevant receptor sites in the brain of the subject, and to elicit neuropharmacological effects (e.g., elicit neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the reoccurrence of the symptoms of the disorder.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to activate relevant receptors to effect neurotransmitter (e.g., dopamine) release but the amount should be insufficient to induce effects on skeletal muscles and ganglia to any significant degree. The effective dose of compounds will of course differ from patient to patient but in general includes amounts starting where CNS effects or dopamine release are first observed in the patient being treated, but below the amount where muscular effects are observed.

Typically, the effective dose of compounds generally requires administering the compound in an amount of less than 1 ug/kg of patient weight. Often, the compounds of the present invention are administered in an amount from 10 ng to less than 1 ug/kg of patient weight, frequently between about 0.1 ug to less than 1 ug/kg of patient weight, and preferably between about 0.1 ug to about 0.5 ug/kg of patient weight. Compounds of the present invention can be administered in an amount of 0.3 to 0.5 ug/kg of patient weight. For compounds of the present invention that do not induce effects on muscle or ganglion-type nicotinic receptors at low concentrations, the effective dose is less than 50 ug/kg of patient weight; and often such compounds are administered in an amount from 0.5 ug to less than 50 ug/kg of patient weight. The foregoing effective doses typically represent that amount administered as a single dose, or as one or more doses administered over a 24 hour period.

For human patients, the effective dose of typical compounds generally requires administering the compound in an amount of at least about 1, often at least about 10, and frequently at least about 25 ug/24 hr./patient. For human patients, the effective dose of typical compounds requires administering the compound which generally does not exceed about 500, often does not exceed about 400, and frequently does not exceed about 300 ug/24 hr./patient. In addition, administration of the effective dose is such that the concentration of the compound within the plasma of the patient normally does not exceed 500 ng/ml, and frequently does not exceed 100 ng/ml.

The compounds useful according to the method of the present invention have the ability to pass across the blood-brain barrier of the patient. As such, such compounds have the ability to enter the central nervous system of the patient. The log P values of typical compounds, which are useful in carrying out the present invention are generally greater than about 0, often are greater than about 0.5, and frequently are greater than about 1.5. The log P values of such typical compounds generally are less than about 4, often are less than about 3.5, and frequently are less than about 3.0. Log P values provide a measure of the ability of a compound to pass across a diffusion barrier, such as a biological membrane. See, Hansch, et al., *J. Med. Chem.* 11:1 (1968).

The compounds useful according to the method of the present invention have the ability to bind to, and in most circumstances, cause activation of, nicotinic dopaminergic receptors of the brain of the patient. As such, such compounds have the ability to express nicotinic pharmacology, and in particular, to act as nicotinic agonists. The receptor binding constants of typical compounds useful in carrying out the present invention generally exceed about 0.1 nM, often exceed about 1 nM, and frequently exceed about 10 nM. The receptor binding constants of such typical compounds generally are less than about 1 M, often are less than about 100 nM, and frequently are less than about 2 nM. Receptor binding constants provide a measure of the ability of the compound to bind to half of the relevant receptor sites of certain brain cells of the patient. See, Cheng, et al., *Biochem. Pharmacol.* 22:3099 (1973).

The compounds useful according to the method of the present invention have the ability to demonstrate a nicotinic function by effectively eliciting neurotransmitter secretion from nerve ending preparations (i.e., synaptosomes). As such, such compounds have the ability to cause relevant neurons to release or secrete acetylcholine, dopamine, and other neurotransmitters. Generally, typical compounds useful in carrying out the present invention provide for the secretion of dopamine in amounts of at least one third, typically at least about 10 times less, frequently at least about 100 times less, and sometimes at least about 1,000 times less, than those required for activation of muscle or ganglion-type nicotinic receptors. Certain compounds of the present invention can provide secretion of dopamine in an amount which can exceed that elicited by an equal molar amount of (S)-(–)-nicotine.

The compounds of the present invention, when employed in effective amounts in accordance with the method of the present invention, are selective to certain relevant nicotinic receptors, but do not cause significant activation of receptors associated with undesirable side effects at concentrations at least 10 times higher than those required for activation of dopamine release. By this is meant that a particular dose of compound resulting in prevention and/or treatment of a CNS disorder, is essentially ineffective in eliciting activation of certain ganglionic-type nicotinic receptors at concentration higher than 5 times, preferably higher than 100 times, and more preferably higher than 1,000 times, than those required for activation of dopamine release. This selectivity of certain compounds of the present invention against those receptors responsible for cardiovascular side effects is demonstrated by a lack of the ability of those compounds to activate nicotinic function of adrenal chromaffin tissue at concentrations at least 10 times greater than those required for activation of dopamine release.

Compounds of the present invention, when employed in effective amounts in accordance with the method of the present invention, are effective towards providing some degree of prevention of the progression of CNS disorders, amelioration of the symptoms of CNS disorders, an amelioration to some degree of the reoccurrence of CNS disorders. However, such effective amounts of those compounds are not sufficient to elicit any appreciable side effects, as demonstrated by increased effects relating to the cardiovascular system, and effects to skeletal muscle. As such, administration of certain compounds of the present invention provides a therapeutic window in which treatment of certain CNS disorders is provided, and side effects are avoided. That is, an effective dose of a compound of the present invention is sufficient to provide the desired effects upon the CNS, but is insufficient (i.e., is not at a high enough level) to provide undesirable side effects. Preferably, effective administration of a compound of the present invention resulting in treatment of CNS disorders occurs upon administration of less than ⅕, and often less than 1/10 that amount sufficient to cause any side effects to a significant degree.

The following examples are provided to further illustrate the present invention, and should not be construed as limiting thereof.

EXAMPLE 1

Sample No. 1 is (+/–)-1-aza-2-(3-pyridyl)bicyclo[2.2.2] octane which is prepared in accordance with the techniques set forth in U.S. Pat. No. 5,559,124, the disclosure of which is incorporated herein by reference in its entirety.

EXAMPLE 2

Sample No. 2 is (+/–)-5-(1-azabicyclo[2.2.2]oct-2-yl)-3-bromo)pyridine, which is prepared in accordance with the following techniques.

Tetrahydropyranyl-4,4-diethylcarboxylate: Sodium (20.7 g, 900 mmol) was dissolved in dry ethanol (300 ml); to this mixture was added diethyl malonate (144 g, 900 mmol) and 2,2-dichlorodiethylether (128.64 g, 900 mmol). The reaction mixture was refluxed for 15 hours and cooled to room temperature. The solvent was removed on a rotary evaporator, the product acidified with 10% HCl (200 ml), extracted with ethyl acetate (4×200 ml), and dried over anhydrous sodium sulfate. Removal of solvent on a rotary evaporator, followed by distillation (170–175° C., 22 mm Hg) furnished the product (98.0 g, 48% yield).

Tetrahydropyranyl-4,4-dicarboxylic acid: To a stirred solution of diester tetrahydropyranyl4,4-diethylcarboxylate (40.00 g., 173 mmol) in ethanol (100 ml) was added potassium hydroxide (21.43 g, 382 mmol) in ethanol (300 ml). After the completion of the addition, the reaction mixture was stirred for 15 minutes at ambient temperature and then refluxed for 2.5 hours. Water (40 ml) was added to the thick, white suspension, and solvent was removed on a rotary evaporator. Water (40 ml) was added to the remaining residue and the resulting mixture then acidified with concentrated sulfuric acid (20 ml). The acidic solution was extracted with diethyl ether (3×300 ml), and the combined organic layers were dried over anhydrous sodium sulfate. Removal of solvent on a rotary evaporator yielded the product (27.3 g, 90.17% yield).

Tetrahydropyranyl-4-carboxylic acid: Tetrahydropyranyl-4,4-dicarboxylic acid was taken in a round bottom flask fitted with a reflux condenser and was gradually heated to 180° C. When evolution of carbon dioxide decreased, the reaction was allowed to cool to room temperature. The mono acid thus obtained was purified by distillation (160–165° C. at 22 mm Hg) to yield tetrahydropyranyl-4-carboxylic acid (16.1 g, 71.8% yield).

Tetrahydropyran-4-methanol: To a stirred solution of lithium aluminum hydride (13.99 g, 368 mmol) in dry tetrahydrofuran (50 ml) was added dry tetrahydrofuran (50 ml), and tetrahydropyranyl-4-carboxylic acid (15.96 g, 123 mmol). The reaction mixture was refluxed for 24 hours then cooled to 0° C., and a solution of sodium hydroxide (30%, 25 ml) was added drop-wise. The solid thus obtained was filtered off, and repeatedly washed with tetrahydrofuran. The filtrate was dried over anhydrous sodium carbonate. Removal of solvent followed by purification over a silica gel column furnished the pyranyl alcohol, tetrahydropyran-4-methanol (13.1 g, 91% yield).

Tetrahydropyranyl-4-methansulfonate ester: To a stirred solution of tetrahydropyranyl-4-methanol (13.0 g, 122 mmol), in dichloromethane (50 ml) was added triethylamine (20.41 g, 201 mmol) in dichloromethane (100 ml) followed by drop-wise addition of mesyl chloride (19.25 g, 168 mmol) at 0° C. and the reaction mixture was stirred for 1 hour at 0° C. and then at room temperature for 14 hours. The reaction mixture was poured into a saturated solution of sodium bicarbonate (100 ml), extracted with dichloromethane (200 ml), dried over anhydrous sodium sulfate followed by removal of solvent on a rotary evaporator and purification over silica gel column chromatography to afford tetrahydropyranyl-4-methanol methanesulfonate ester (13.9 g, 63.8% yield).

3-Bromo-5-hydroxymethylpyridine: 3-Bromo-5-hydroxymethylpyridine can be prepared according to either of two techniques.

Method A: Ethyl 5-bromo-3-nicotinate is prepared by dissolving 5-bromo-3-nicotinic acid (50 g, 247.5 mmol) in ethyl alcohol (130 ml) at room temperature. To this solution was added drop-wise concentrated sulfuric acid (50 ml, 938 mmol) with constant stirring. After completion of the addition, the reaction mixture was refluxed for 40 hours and cooled to 0° C., followed by neutralization with saturated sodium carbonate solution (pH=8). The neutralized solution was extracted with chloroform (3×200 ml), and dried over anhydrous sodium sulfate. Removal of solvent on a rotary evaporator furnished ethyl 5-bromo-3-nicotinate (39.85 g, 97% yield).

Ethyl 5-bromo-3-nicotinate is reduced by adding sodium borohydride (29.6 g., 782.6 mmol) to a stirred solution of ethyl 5-bromo-3-nicotinate (20 g, 86.9 mmol) in ethyl alcohol (450 ml). The reaction mixture was refluxed for 30 hours, then the solvent was removed on a rotary evaporator. The solid thus obtained was treated with 10% dilute hydrochloric acid (3N, 40 ml) to pH6, and the resulting aqueous solution extracted with ethyl acetate (3×200 ml), and dried over nhydrous sodium sulfate. Removal of solvent followed by purification over silica gel column chromatography furnished 3-bromo-5-hydroxymethyl pyridine (8.5 g, 52% yield).

Method B: To a suspension of 5-bromonicotinic acid (1 g, 4.9 mmol) in benzene (20 ml) was added triethylamine (0.73 ml, 5.2 mmol) at room temperature. After stirring for 5 minutes, ethyl chloroformate (0.5 ml, 5.2 mmol) was added, and the mixture was stirred for a further 1 hour at room temperature. The triethylamine hydrochloride salt thus precipitated, was filtered off, and the filtrate was evaporated to dryness to give the mixed anhydride, which was not isolated, but taken up in dry tetrahydrofuran (26 ml), and the solution immediately added to a stirred suspension of lithium aluminum hydride (0.2 g, 5.29 mmol) in dry tetrahydrofuran (7 ml) at −78° C. This mixture was stirred for 30 min. at −78° C. Workup in the usual manner, followed by purification over silica gel column chromatography yielded 3-bromo-5-hydroxymethylpyridine (0.762 g, 82% yield).

5-Bromo-3-pyridinemethanamine: 5-Bromo-3-pyridinemethanamine can be prepared according to either of two techniques.

Method A: 5-Bromo-3-N-(phthalimidomethyl)-pyridine is produced by adding triphenylphosphine (12.1 g, 46.3 mmol) and phthalimide (6.8 g, 46.3 mmol) in dry tetrahydrofuran (70 ml) to a stirred suspension of 3-bromo-5-hydroxymethylpyridine (6.7 g, 35.6 mmol), and then adding DEAD (7.3 ml, 46.3 mmol) in dry tetrahydrofuran (30 ml) drop-wise. The reaction mixture was stirred at room temperature overnight. After removal of the solvent on a rotary evaporator, the crude material was purified by column chromatography over silica gel to yield the product (9.5 g, 85% yield).

5-Bromo-3-N-(phthalimidomethyl)-pyridine is (7 g, 25 mmol) then hydrolyzed by treatment with aqueous methylamine (40%, 50 ml), and refluxing the mixture for 3 hours. Solvent was removed on a rotary evaporator to yield a pale-yellow colored solid, which was then taken up into concentrated hydrochloric acid (50 ml) and the solution refluxed for 15 hours. The reaction mixture was basified (pH =10–11) with aqueous sodium hydroxide (50%), extracted with chloroform (5×40 ml), and dried over anhydrous potassium carbonate. The solvent was removed on a rotary evaporator and the product purified by column chromatography over silica gel to yield 5-bromo-3-pyridinemethanamine (2.8 g, 67.97% yield).

Method B: 3-Bromo-5-hydroxymethylpyridine (1.1 g, 5.8 mmol) was added to thionyl chloride (5 ml) at 0° C. under nitrogen over 5 minutes. The solution was stirred at room temperature for 1 hour, re-cooled to 0° C., and dry ether (40 ml) was added. The resulting solid was filtered off, washed with ether and added to a stirred solution of ammonia (28%, 30 ml) and ethyl alcohol (40 ml) at 0° C. The solution was then stirred at room temperature for 20 hours. The solvent was removed on a rotary evaporator, and the crude material partitioned between sodium hydroxide (2N, 30 ml) and dichloromethane (60 ml). The organic layer was dried over anhydrous sodium sulfate, the solvent removed and the residue purified by flash chromatography over silica gel using $CHCl_3$/ethanol/concentrated aqueous ammonia solution (100:6:1) as eluent to afford 5-bromo-3-pyridinemethanamine (785 mg, 72% yield).

5-Bromo-N-(diphenylmethylidene)-3-(aminomethyl)-pyridine: To a solution of 5-bromo-3-pyridinemethanamine 10 (1.5 g, 8.02 mmol) in dry toluene (5 ml), was added benzophenone (1.6 g, 8.79 mmol) and p-toluene sulfonic acid (PTSA, 2 mg). The reaction mixture was refluxed for 48 hours using a Dean-Stark apparatus. After the completion of the reaction, the solvent was removed in vacuum and the crude material was purified through silica gel column chromatography to yield 5-bromo-N-(diphenylmethylidene)-3-(aminomethyl)-pyridine (1.9 g, 56% yield).

1-Amino-1-[3-(5-bromopyridyl)]-2-(4-tetrahydropyrano)-ethane: To a solution of diisopropyl amine (0.55 m., 3.92 mmol) in dry tetrahydrofuran (3 ml) was added n-butyl lithium (2.45 ml, 1.6 M solution in tetrahydrofuran) at 0° C.; this mixture was then added to a stirred suspension of Schiff base, 5-bromo-N-(diphenylmethylidene)-3-(aminomethyl)-pyridine (1.00 g, 3.01 mmol) in dry tetrahydrofuran (10 ml) at −78° C., LDA (0.5 ml, 3.92 mmol) was added through a cannula, and the reaction mixture was stirred for 45 minutes at 78° C. Tetrahydropyranyl-4-methanol methanesulfonate ester (0.706 g, 3.92 mmol) in dry tetrahydrofuran at −78° C. was then added to the lithiated Schiff base. The reaction mixture was allowed to warm to ambient temperature followed by additional stirring for 12 hours. The reaction mixture was quenched with hydrochloric acid (10% w/v, 20 ml) and stirred for 30 minutes, followed by extraction with ethyl acetate (3×25 ml). The resulting aqueous solution was made basic (pH=8–9) by adding solid potassium carbonate, and the mixture extracted with chloroform (3×25 ml). The combined organic layers were dried over anhydrous potassium carbonate. Removal of solvent on a rotary evaporator and purification of the residue by silica gel column chromatography furnished 1-amino-1-[3-(5-bromopyridyl)]-2-(4-tetrahydropyrano)-ethane as a pale-yellow colored syrup which could not be distilled (600 mg, 70% yield).

(+/−)-5-(1-azabicyclo[2.2.2oct-2-yl)-3-(bromo)pyridine dihydrochloride: 1-Amino-1-[3-(5-bromopyridyl)]-2-(4-tetrahydropyrano)-ethane (12) (500 mg, 1.76 mmol) was dissolved in aqueous hydrobromic acid (48%, 10 ml) and hydrogen bromide gas was passed through the solution until saturated. The reaction mixture was then carefully transferred to a pressure tube and heated at 120° C. for 16 hours. The reaction mixture was allowed to cool to ambient temperature, and was then transferred to a round bottom flask. HBr was removed on a rotary evaporator. The resulting dark brown residue was taken up into absolute ethanol and the solution heated with potassium carbonate (3 g) for 12 hours. The reaction mixture was cooled to room temperature and filtered through a celite pad. Removal of solvent followed by purification of the resulting residue over silica gel column chromatography, yielded the product (150 mg, 32% yield).

5-(1-azabicyclo[2.2.2]oct-2-yl-3-(bromo)pyridine free base (90 mg, 0.33 mmol) was dissolved in ethanolic HCl (5 ml) and the mixture sonicated for 5 minutes. The solvent was removed on a rotary evaporator to yield a solid residue which was recrystallized from isopropanol to afford the dihydrochloride salt as a light brown crystalline solid (100 mg).

EXAMPLE 3

Sample No. 3 is exo 1-aza-2-(3-pyridyl)bicyclo[2.2.1] heptane, which is prepared according to the following techniques.

N-(diphenylmethylidene)-3-(aminomethyl)pyridine: Benzophenone (10.92 g, 60 mmol), 3-(aminomethyl) pyridine (6.48 g, 60 mmol) and p-toluenesulfonic acid (10 mg) were dissolved in 30 mL benzene, and the reaction mixture was heated to reflux under a nitrogen atmosphere with a Dean-Stark trap. The completion of the reaction (12–16 hours) was determined after the calculated amount of water was collected in the Dean-Stark trap. Benzene was removed on a rotary evaporator and the resulting Schiff base was used in the next step without further purification.

Tetrahydro-3-furanmethanol methanesulfonate: Methanesulfonyl chloride (18 mmol, 1.39 mL) was added to a flask containing (±)-tetrahydro-3-furanmethanol (1.53 g, 15.0 mmol) in tetrahydrofuran (25 mL) and triethylamine (3.13 mL, 22.5 mmol) at 0° C. under a nitrogen atmosphere. The cooling bath was removed and the reaction mixture was stirred overnight. A saturated solution of $NaHCO_3$ (15 mL) was added to the reaction mixture followed by extraction with diethyl ether (3×15 mL). The combined organic extracts were dried over anhydrous magnesium sulfate. Filtration followed by concentration on a rotary evaporator yielded the product as a pale yellow solid (2.13 g) which was used in the next step without further purification.

1-Amino-1-(3-pyridyl)-2-(3-tetrahydrofuranyl)-ethane: LDA (14.66 mmol) was generated at 0° C. by adding n-BuLi (6.4 mL of 2.3 M solution in hexane, 14.66 mmol) to a solution of diisopropylamine (2.27 mL, 16.0 mmol) in dry tetrahydrofuran (THF) (13 mL). N-(diphenylmethylidene)-3-(aminomethyl)pyridine (3.62 g, 13.33 mmol) was dissolved in dry tetrahydrofuran (13 mL) and the solution cooled to −78° C. under a nitrogen atmosphere. LDA was then transferred to the solution of N-(diphenylmethylidene)-3-(aminomethyl)pyridine using a double tipped needle under a positive nitrogen atmosphere. The resulting purple suspension was stirred for a further 45 minutes, during which time the temperature of the reaction mixture was allowed to rise to −4° C. Tetrahydro-3-furanmethanol methanesulfonate (2.64 g, 14.7 mmol) in tetrahydrofuran (10 mL) was then added via a syringe and the reaction mixture was allowed to warm to ambient temperature followed by additional stirring for 12 hours. Hydrochloric acid (10% aq., 20 mL) was added, and the reaction mixture was stirred for 20–30 minutes followed by extraction with ethyl acetate (3×25 mL). The resulting aqueous solution was first made basic by adding solid $K_2CO_3$, and then extracted with chloroform (3×25 mL). The combined organic extracts were dried over anhydrous $K_2CO_3$. Filtration was followed by evaporation of chloroform to yield 1-amino-1-(3-pyridyl)-2-(3-tetrahydrofuranyl)-ethane as a diastereomeric (50:50) mixture (pale yellow oil, 2.03 g) which was used in the next step without further purification.

Exo-1-aza-2-(3-pyridyl)bicyclo[2.2.1]heptane: 1-Amino-1-(3-pyridyl)-2-(3-tetrahydrofuranyl)-ethane (960 mg, 5 mmol) was dissolved in hydrobromic acid (aq., 48%, 12 mL). Hydrogen bromide gas was generated according to the procedure described in Vogel's Textbook of Practical Organic Chemistry, 5th ed., Longman Scientific & Technical, 1991, pp 437–438, by dropwise addition of bromine to tetralene, and the HBr gas thus generated was passed through the acidic solution of 1-amino-1-(3-pyridyl)-2-(3-tetrahydrofuranyl)-ethane until saturated. The solution was then carefully transferred to a pressure tube and heated at 100° C. under pressure for 12–16 hours. The tube was allowed to cool to ambient temperature and the contents then transfered to a round bottom flask. The mixture was basified with solid $K_2CO_3$ followed by stirring for 2 hours. The reaction mixture was then extracted with chloroform (3×15 mL). The combined organic extracts were dried over anhydrous $K_2CO_3$. Filtration, followed by removal of solvent on a rotary evaporator yielded 700 mg of product as a dark brown oil. Separation of the endo and exo isomers in the product was achieved by silica gel column chromatography using 15% (v/v) methanol in chloroform as the eluting solvent. The fractions with $R_f$ value 0.43 (on analytical silica plates with 15% (v/v) methanol in chloroform as the eluting solvent) were concentrated on a rotary evaporator to obtain exo-1-aza-2-(3-pyridyl)bicyclo[2.2.1]heptane as a pale brown oil (190 mg) which was distilled under vacuum (92–95° C.) at 0.0025 mm Hg) to obtain 115 mg (13.2%) of colorless oil.

EXAMPLE 4

Sample No. 4 is endo -1-aza-2-(3-pyridyl)bicyclo[2.2.1] heptane which is isolated as follows:

The fractions from Example 3 containing the endo isomer with an $R_f$ value of 0.33 (on analytical silica plates with 15% (v/v) methanol in chloroform as the eluting solvent) were concentrated on a rotary evaporator to afford endo-1-aza-2-(3-pyridyl)bicyclo[2.2.1]heptane as a pale brown oil, which was distilled (101 to 104° C. at 0.0025 mm Hg) to obtain 80 mg of pure endo-1-aza-2-(3-pyridyl)bicyclo[2.2.1]heptane (9.1%) as a colorless oil.

EXAMPLE 5

Sample No. 5 is 1-aza-7-(3-pyridyl)bicyclo[2.2.1]heptane which was prepared according to the following techniques.

1-Amino-1-(3-pyridyl)-1-(4-tetrahydropyranyl)-methane: The methaneamine derivative was synthesized essentially according to the procedure described for the synthesis of 1-amino-1-(3-pyridyl)-2-(3-tetrahydrofuranyl)-ethane. Thus, tetrahydropyran-4-ol methane sulfonate (0.99 g, 5.5 mmol), prepared according to the procedure of Suto et al., *J. Med. Chem.,* 34:2484 (1991), was treated with the imine anion generated by reacting N-(diphenylmethylidene)-3-(aminomethyl)pyridine (1.36 g, 5.0 mmol) with LDA (5.5 mmol in 5.0 mL tetrahydrofuran). A work up similar to the one described for the synthesis of 1-amino-1-(3-pyridyl)-2-(3-tetrahydrofuranyl)-ethane, followed by purification by column chromatography (15% methanol in chloroform) yielded 1-amino-1-(3-pyridyl)-1-(4-tetrahydropyranyl)-methane (499 mg) in 52% yield.

1-aza-7-(3-pyridyl)bicyclof2.2.1.]heptane: Treatment of 1-amino-1-(3-pyridyl)-1-(4-tetrahydropyranyl)-methaneamine (576 mg, 3 mmol) with hydrobromic acid, as described for the synthesis of the 1-aza-2-(3-pyridyl)bicyclo [2.2.1]heptanes resulted in formation of the product, as a dark brown oil which was purified by column chromatography (15% methanol in chloroform), followed by distillation (90° C. at 0.005 mm Hg) under reduced pressure to obtain the product as a colorless oil (260 mg, 51% from 1-amino-1-(3 -pyridyl)-1-(4-tetrahydropyranyl)-methane.

EXAMPLE 6

Sample No. 6 is 5-(1-azabicyclo[2.2.2]oct-2-yl-3-(amino) pyridine trihydrochloride, which is prepared in accordance with the following techniques.

5-(1-azabicyclo[2.2.2]oct-2-yl)-3-(bromo)pyridine (120 mg), was mixed with aqueous ammonium hydroxide (20 mL, 28%) in a sealed tube, copper sulfate (200 mg) was added, and the reaction mixture was heated at 180° C. for 14 hours. The reaction mixture was allowed to cool to ambient temperature and then extracted with chloroform (4×20 mL). The combined organic extracts were dried over anhydrous potassium carbonate, filtered, and the solvent removed on a rotary evaporator to afford a dark syrup. This crude product was subjected to column chromatography over silica gel using chloroform:methanol:triethylamine (9:1:1) to yield an initial fraction of 5-(1-azabicyclo[2.2.2]oct-2-yl)-3-(amino) pyridine, which after removal of solvent afforded a light brown solid (20 mg) homogeneous on TLC (silica, chloroform:methanol 95:5). An impure fraction was also obtained, which afforded a brown solid (40 mg), found to be mostly the desired compound with minor impurities on TLC analysis (total yield ~65%).

5-(1-azabicyclo[2.2.2]oct-2-yl)-3-(amino)pyridine free base (20 mg, 0.98 mmol) was dissolved in ethanolic HCl (2 mL) and the mixture sonicated for 5 minutes. The solvent was removed on a rotary evaporator to yield a viscous oil, which solidified, to afford the trihydrochloride salt of the product as a brown colored solid (20 mg from ethanol/ether (9:1), mp 210° C. with decomposition.

EXAMPLE 7

Sample No. 7 is 5-(1-azabicyclo[2.2.2]oct-2-yl)-3-(ethoxy)pyridine dihydrochloride, which is prepared according to the following techniques.

To a stirred solution of 5-(1-azabicyclo[2.2.2]oct-2-yl)-3-(amino)pyridine trihydrochloride (25 mg, 0.08 mmol) in dry ethanol (3 mL) was added isoamyl nitrite (0.1 mL, 0.742 mmol) and the mixture was refluxed for 2 h. When TLC analysis of the reaction mixture showed absence of starting material, the heating was stopped and the mixture was allowed to cool to ambient temperature. The solvent then was removed on a rotary evaporator to yield a thick brown oil, which solidified upon addition of dry diethyl ether. The product thus obtained was dissolved in chloroform and kept overnight at 4° C. to induce crystallization. The resulting solids were filtered, washed with diethyl ether and finally dried under vacuum for 24 h, to yield the product in the form of a dihydrochloride salt (10 mg, 51.4%) as colorless needles.

EXAMPLE 8

Sample No. 8 is 5-(1-azabicyclo[2.2.2]oct-2-yl-3-(isopropyloxy)pyridine dihydrochloride, which is prepared according to the following techniques.

To a stirred solution of 5-(1-azabicyclo[2.2.2]oct-2-yl)-3-(amino)pyridine trihydrochloride (50 mg, 0.16 mmol) in dry isopropanol (5 mL) was added isoamyl nitrite (0.1 mL, 0.97 mmol) and the reaction mixture was refluxed for 2 h. When TLC analysis of the reaction mixture showed the absence of starting material, the heating was stopped, and the solvent was removed under vacuum. A white solid was obtained upon the addition of dry diethyl ether. The solid was dissolved with heating in a minimum amount of chloroform, and the solution kept over night at 4° C. to induce crystallization of the dihydrochloride salt. The compound thus obtained was filtered and dried under vacuum for 24 h, to afford the dihydrochloride salt of the product (28 mg, 55%) as colorless needles.

Comparison Example

For comparison purposes, Sample No. C-1 is (S)-(−)-nicotine, which has been reported to have demonstrated a positive effect toward the treatment of various CNS disorders.

EXAMPLE 9

Determination of Log P Value

Log P values, which have been used to assess the relative abilities of compounds to pass across the blood-brain barrier (Hansch, et al., *J. Med. Chem.* ii:1 (1968)), were calculated according using the Cerius$^2$ software package Version 3.0 by Molecular Simulations, Inc. Log P values are reported in Table 1 below.

EXAMPLE 10

Determination of Binding to Relevant Receptor Sites

Binding of the compounds to relevant receptor sites was determined in accordance with the techniques described in U.S. Pat. No. 5,597,919 to Dull et al. Inhibition constants (Ki values), reported in nM, were calculated from the IC$_{50}$ values using the method of Cheng et al., *Biochem, Pharmacol.* 22:3099 (1973). The results are reported in Table 1 below.

EXAMPLE 11

Determination of Dopamine Release

Dopamine release was measured using the techniques described in U.S. Pat. No. 5,597,919 to Dull et al. Release is expressed as a percentage of release obtained with a concentration of (S)-(−)-nicotine resulting in maximal effects. Reported EC$_{50}$ values are expressed in nM, and E$_{max}$ values represent the amount released relative to (S)-(−)-nicotine on a percentage basis. The results are reported in Table 1 below.

EXAMPLE 12

Determination of Interaction with Muscle Receptors

The determination of the interaction of the compounds with muscle receptors was carried out in accordance with the techniques described in U.S. Pat. No. 5,597,919 to Dull et al. The maximal activation for individual compounds (E$_{max}$) was determined as a percentage of the maximal activation induced by (S)-(−)-nicotine. Reported EC$_{50}$ values are reported in nM, and E$_{max}$ values represent the amount released relative to (S)-(−)-nicotine on a percentage basis. The results are reported in Table 1 below.

EXAMPLE 13

Determination of Interaction with Ganglion Receptors

The determination of the interaction of the compounds with ganglionic receptors was carried out in accordance with the techniques described in U.S. Pat. No. 5,597,919 to Dull et al. The maximal activation for individual compounds ($E_{max}$) was determined as a percentage of the maximal activation induced by (S)-(−)-nicotine. Reported $EC_{50}$ values are reported in nM, and $E_{max}$ values represent the amount released relative to (S)-(−)-nicotine on a percentage basis. The results are reported in Table 1 below.

TABLE 1

| Sample No. | Log P | Ki(nM) | Dopamine Release | | Muscle Effect | | Ganglion Effect | |
|---|---|---|---|---|---|---|---|---|
| | | | $EC_{50}$ | $Ec_{max}$ | $EC_{50}$ | $Ec_{max}$ | $EC_{50}$ | $Ec_{max}$ |
| 1 | 1.26 | 2 | 2 | 40 | 59 | 110 | 1,100 | 85 |
| 2 | 2.05 | 1 | 2 | 43 | 3,000 | 133 | 3,000 | 106 |
| 3 | 0.94 | 0.5 | 6 | 130 | 100 | 130 | 150 | 100 |
| 4 | 0.94 | 2.5 | 33 | 114 | 100 | 130 | 150 | 100 |
| 5 | 0.93 | 7 | 4 | 93 | 300 | 130 | N/A | 120 |
| 6 | 0.48 | 2.6 | 7 | 43 | 3,000 | 100 | 10,000 | 75 |
| 7 | 1.82 | 1 | 5 | 40 | 700 | 137 | 10,000 | 86 |
| 8 | 1.76 | 0.4 | 31 | 31 | 3,000 | 115 | 10,000 | 94 |
| C-1* | 0.71 | 2 | 115 | 100 | 60,000 | 100 | 20,000 | 100 |

*Not an example of the invention.
N/A Not available.

The data in Table 1 indicate that the compounds of the present invention have the capability to selectively bind with high affinity to certain CNS nicotinic receptors as indicated by their low binding constants, and their ability to selectively activate certain CNS receptors and cause neurotransmitter release, as evidenced by dopamine release, thereby demonstrating known nicotinic pharmacology. The data further indicate that certain compounds activate dopamine release at concentrations well below those concentrations required for activation of muscle or ganglionic receptors. Thus, the data indicate that the compounds of the present invention have the capability of being useful in treating CNS disorders involving nicotinic cholinergic systems. Furthermore, the data indicate that certain compounds of the present invention do not cause any appreciable side effects at muscle sites and ganglionic sites at concentrations effective for producing CNS effects or neurotransmitter release, thus indicating a lack of undesirable side effects in subjects receiving administration of those compounds at dose ranges at which CNS effects and neurotransmitter release are elicited.

The data indicate that the compounds of the present invention have the capability to activate human CNS receptors without activating muscle-type or ganglionic-type nicotinic acetylcholine receptors. The data show that the compounds of the present invention provide a therapeutic window for utilization in the treatment of CNS disorders. That is, at the levels that the compounds of the present invention are employed, those compounds show CNS effects and/or neurotransmitter release effects to a significant degree but do not show undesirable muscle or ganglionic effects to any significant degree. The data show that certain compounds of the present invention, particularly Sample Nos. 2, 6 and 8, begin to cause muscle effects and effects upon ganglia only when employed in amounts of many times those required to cause dopamine release.

The foregoing is illustrative of the present invention and is not to be construed as limiting thereof. The invention is defined by the following claims, with equivalents of the claims to be included therein.

That which is claimed is:

1. A method for treating a disorder characterized by alteration in normal, neurotransmitter release comprising administering to a subject in need thereof an effective, amount of a compound of the general formula:

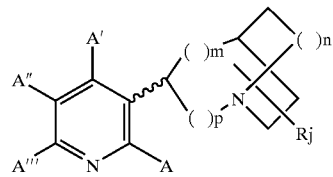

wherein
A, A', A" and A'" individually are substituent species selected from the group consisting of H, halo, R', —NR'R", —CF$_3$, —OH, —CN, —NO$_2$, —C$_2$R', —SH, —SCH$_3$, —N$_3$, —SO$_2$CH$_3$, —OR', —SR', —C(=O)NR'R", —NR'C(=O)R', —C(=O)R', —C(=O)OR', —(CH$_2$)$_q$OR', —OC(=O)R', —OC(=O)NR'R" and —NR'C(=O)OR',
R' and R" are individually hydrogen, lower alkyl, an aromatic group-containing species, or a substituted aromatic group-containing species,
the substituents on the substituted aromatic group-containing species are as identified above with respect to A, A', A" and A'",
the aromatic-group containing species is pyridinyl, quinolinyl, pyrimidinyl, phenyl or benzyl,
q is an integer from 1 to 6,
m, n and p are individually 0, 1 or 2, and the sum of p plus m is 1 or 2, when n is o; j is an integer from 0 to 5, wherein (m+n+p)=1 or 3,
R is a non-hydrogen substituent selected from the same group of substituents as listed above with respect to A, A', A" and A'"; and the wavy line in, the structure represents that, depending upon the value of each of m, n, p and j, the compound, can have an endo or exo form.

2. A method for treating a central nervous system disorder comprising, administering to a subject in need thereof, an effective amount of a compound of the general, formula:

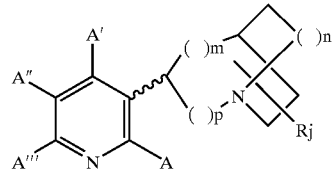

wherein
A, A', A" and A'" individually are substituent species selected from the group consisting of H, halo, R', —NR'R", —CF$_3$, —OH, —CN, —NO$_2$, —C$_2$R', —SH, —SCH$_3$, —N$_3$, —SO$_2$CH$_3$, —OR', —SR', —C(=O)NR'R", —NR'C(=O)R', —C(=O)R', —C(=O)OR', —(CH$_2$)$_q$OR', —OC(=O)R', —OC(=O)NR'R" and —NR'C(=O)OR',
R' and R" are individually hydrogen, lower alkyl, an aromatic group-containing species, or a substituted aromatic group-containing species,
the substituents on the substituted aromatic group-containing species are as identified above with respect to A, A', A" and A'",
the aromatic-group containing species is pyridinyl, quinolinyl, pyrimidinyl, phenyl or benzyl,
q is an integer from 1 to 6,
m, n and p are individually 0, 1 or 2, and the sum of p plus m is 1 or 2, when n is o; j is an integer from 0 to 5, wherein (m+n+p)=1 or 3, R is a non-hydrogen substituent selected from the same group of substituents as listed above with respect to A, A', A" and A'"; and the wavy line in, the structure represents that, depending upon the value of each of m, n, p and j, the compound, can have an endo or exo form.

3. The method according to claim 1 or 2 wherein j is 0 or 1.

4. The method according to claim 1 or 2 wherein j is 0.

5. The method according to claim 1 or 2 wherein m=1, n=0 and p=0.

6. The method according to claim 1 or 2 wherein m 2, n=1 and p=0.

7. The method according to claim 1 or 2 wherein m=0, n=1 and p=0.

8. The method according to claim 1 or 2 wherein m=1, n=1 and p=1.

9. The method according to claim 1 or 2 wherein m=1, n=2 and p=0.

10. The method according to claim 1 or 2 wherein A, A' and A'" are hydrogen.

11. The method according to claim 1 or 2 wherein the amount effective to treat said disorder is less than 1 ug/kg patient.

* * * * *